(12) United States Patent
Propp et al.

(10) Patent No.: US 7,494,500 B2
(45) Date of Patent: *Feb. 24, 2009

(54) SURGICAL INSTRUMENT WITH SNAG FREE BOX HINGE

(75) Inventors: Donald J. Propp, Dewitt, MI (US); Gary A. Gillis, Ann Arbor, MI (US)

(73) Assignee: Tri-State Hospital Supply Corporation, Howell, MI (US)

( * ) Notice: Subject to any disclaimer, the term of this patent is extended or adjusted under 35 U.S.C. 154(b) by 704 days.

This patent is subject to a terminal disclaimer.

(21) Appl. No.: 10/719,171

(22) Filed: Nov. 21, 2003

(65) Prior Publication Data

US 2004/0106947 A1 Jun. 3, 2004

Related U.S. Application Data

(63) Continuation-in-part of application No. 10/284,519, filed on Oct. 30, 2002, now Pat. No. 7,351,248.

(60) Provisional application No. 60/367,610, filed on Mar. 25, 2002.

(51) Int. Cl.
*A61B 17/28* (2006.01)
(52) U.S. Cl. .......................... 606/205; 81/416; 600/564

(58) Field of Classification Search ................. 600/564; 604/22, 174; 606/205, 206, 207, 208, 210
See application file for complete search history.

(56) References Cited

U.S. PATENT DOCUMENTS 3,763,726 A * 10/1973 Hildebrand .................. 81/416

* cited by examiner

*Primary Examiner*—Kevin T Truong
*Assistant Examiner*—Victor X Nguyen
(74) *Attorney, Agent, or Firm*—Fildes & Outland, P.C.

(57) ABSTRACT

A surgical instrument includes a pair of elongated members joined together by a box hinge. The box hinge is formed of a slot in the first member and a hinge portion in the second member. The hinge portion of the second member is generally the same width as that of the second member on either side of the box hinge. The width of the first elongated member is larger than the width of the second elongated member at either end of the box hinge portion. The first and second box hinge portions have pivot points that mate to allow the hinge to open and close. The pivot points may be corresponding protrusions and depressions of any preferred shape. The unique construction of the box hinge creates a snag-free surface that allows for the use of the instrument for tasks such as suturing without the suturing thread snagging on the instrument.

10 Claims, 4 Drawing Sheets

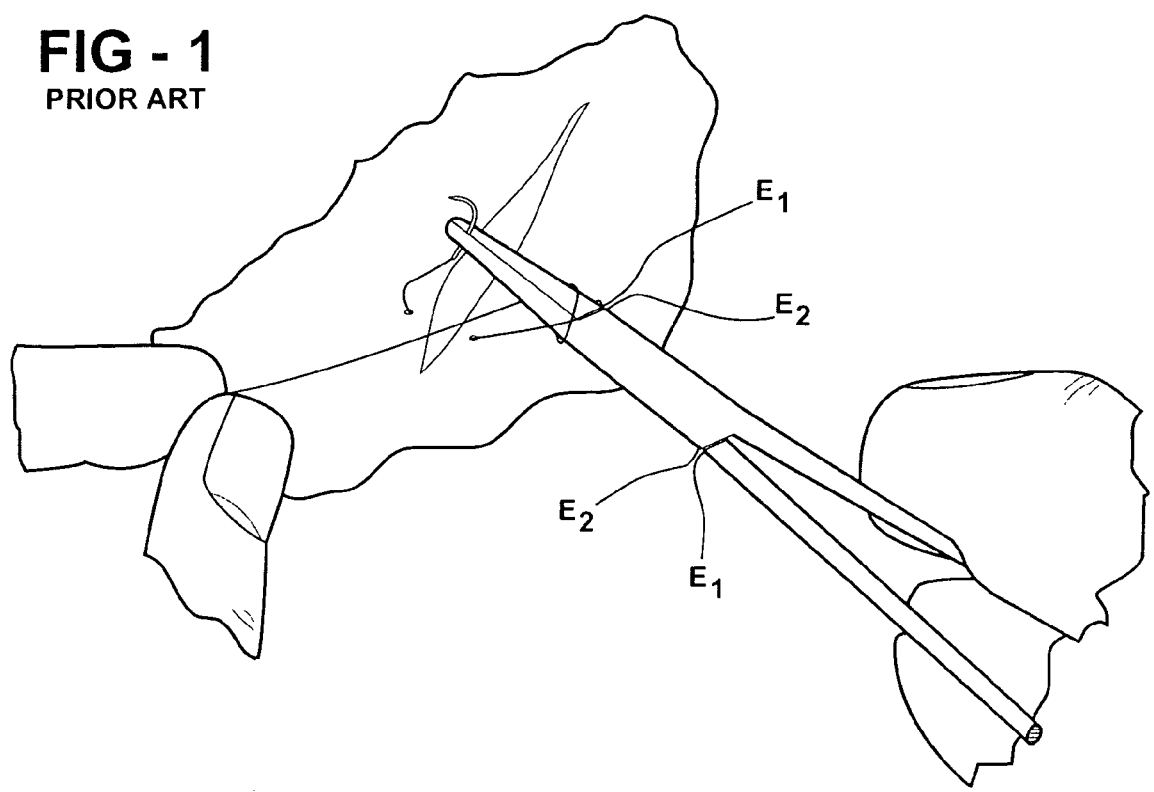
FIG - 1
PRIOR ART
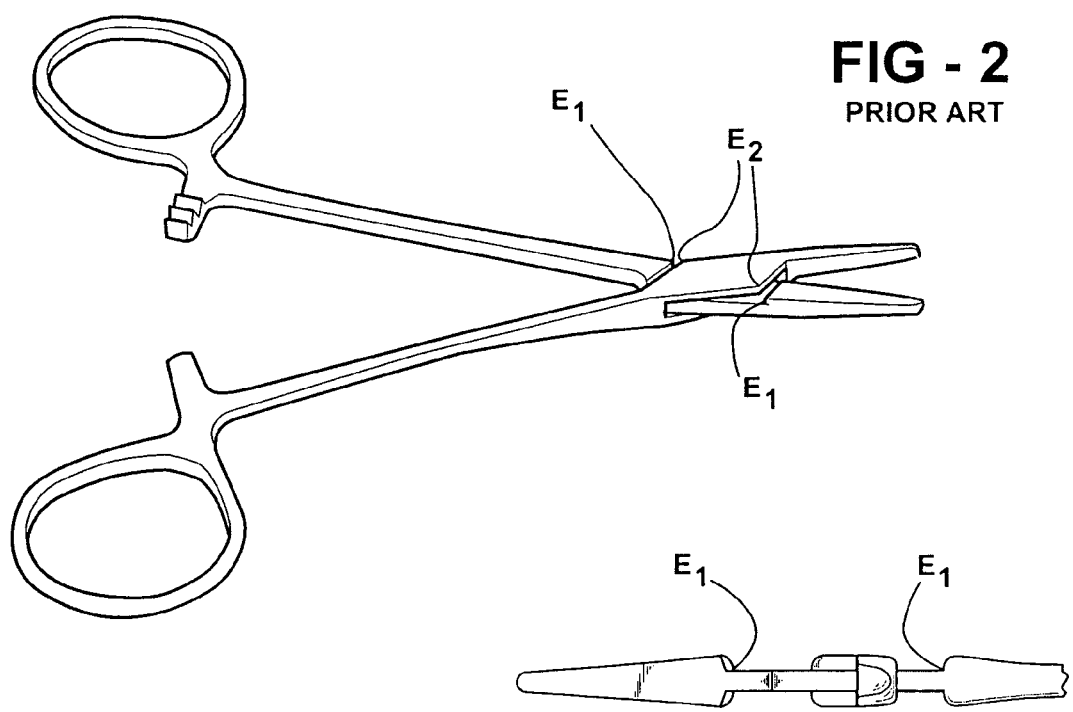
FIG - 2
PRIOR ART
FIG - 3
PRIOR ART

SURGICAL INSTRUMENT WITH SNAG FREE BOX HINGE

CROSS REFERENCE TO RELATED APPLICATION

This application is a continuation-in-part of application Ser. No. 10/284,519, filed on Oct. 30, 2002, now U.S. Pat. No. 7,351,248 which claims the benefit of U.S. Provisional Application No. 60/367,610, filed Mar. 25, 2002.

TECHNICAL FIELD

This invention relates to medical and surgical instruments and more particularly to surgical instruments such as needle holders, forceps, hemostats, clamps, and occluders which incorporate a box-type hinge.

BACKGROUND OF THE INVENTION

Medical and surgical instruments such as needle holders, needle drivers, forceps and occluders that incorporate a box hinge between handle ends and working tip ends are well known. Referring to FIGS. 1 through 3, these instruments include a pair of members joined together by a box hinge. Forming the box hinge one of the members includes a slot having flat, parallel sides and the other member includes a portion machined to conform with the flat, parallel sides of the slot. The machined portion extends through the slot in an assembled instrument. A hinge pin extends through the parallel sides of the slot and through the machined portion of the other member disposed in the slot. It is known that suture thread does snag at or on edges $E_1$ around the machined portion of the one member and around or under machined edges $E_2$ machined around the slot. In an attempt to reduce snags some manufacturers bevel the machined edges, or attempt to provide very expensive and precise matched grinding of the handles at either end of the box hinge where the machined portion first interfaces with the slot.

Even with the beveled edges a suture may snag above and below the pivot point of the hinge as a surgeon is tying a knot in the suture, or when a prior art instrument goes into and out of an array of temporarily placed suture threads placed in, or around, a large wound or opening in tissues; in which one or more layers is held open by multiple instruments and suture threads. Such snagging can occur when preparatory knot loops, or partial turns, are moving either up, or down, the instrument body, and at locations both above, and below, the box hinge. Snagging potential increases directly with smaller suture thread and with larger suture needles (more open jaws and mismatch at the prime snag areas). Likewise, the matched grinding has the disadvantage of being costly typically still snagging when suture thread is of very fine diameter, and still leads to snagging due to mismatch of the interface as the working tip ends are opened slightly to hold the suture needle or other objects.

It is further known in the art relating to medical and surgical instruments that the box hinge of the instrument includes a hinge pin that extends through both members of the instrument. The hinge pin holds the two member of the instrument together while also allowing the two members to rotate relative to each other. Fabrication of an instrument with such a box hinge, however, requires that the hinge pin be driven through both members. This process may cause damage to the pin, requires very precise dimensional control to avoid poor alignment and sloppy feel, requires very fine finish grinding on the outermost surfaces of the box hinge at the two pin end locations, and cosmetically is very difficult to hide the pin ends.

SUMMARY OF THE INVENTION

The present invention provides a box hinge for a medical or surgical instrument that completely eliminates any possibility of snagging a suture on edges of the instrument around the box hinge. The present invention further provides a box hinge that functions without the need for a hinge pin.

Accordingly, interacting surfaces of a snag-free medical or surgical instrument box hinge includes edges having a smooth cooperative transition so that relative movement between the instrument box hinge and a suture is uninterrupted as there are no snag points along edges of the box hinge for the suture to get caught in or on during working movement.

More specifically, a surgical instrument in accordance with the invention includes a pair of elongated members joined together by a box hinge. The box hinge is formed by a slot in the first member and, instead of a machined portion, as in the known art, a hinge portion of generally continuous cross-section in the second member. The hinge portion of the second member conforms and cooperates with the surfaces of the slot. The hinge portion of the second member may be generally the same width as that of the second member on either side of the box hinge, thereby eliminating points where a suture can snag above and below the box hinge. In other words, the hinge portion of the second member preferably has a generally continuous cross sectional shape being generally that of portions of the second member on either end of the hinge portion. Further, the box hinge portion of the first member includes pivot points on the upper and lower sides of the slot. Likewise, the box hinge portion of the second member includes pivot points on the side surfaces, the side surfaces being the surfaces that oppose the upper and lower sides of the slot. The pivot points of the first box hinge portion mate with the pivot points of the second box hinge portion and thereby allow the hinge to open and close.

In an embodiment of the invention the instrument includes two elongated members, each of which comprises a box hinge portion, a handle end portion and a working tip portion. The length of the handle end portion is generally longer than the length of the working tip portion. The handle end portion comprises a circular finger handle and a locking mechanism that holds the box hinge in a closed position. The working tip portion may have working surfaces that include a plurality of ridges, or various other kinds of grasping structure, shapes, and designs.

The box hinge comprises a slot in the box hinge portion of the first elongated member and the box hinge portion of the second elongated member received in the slot. The box hinge portion of the second elongated member conforms to the generally flat surfaces of the slot. The box hinge portion of the first member includes pivot points on the upper and lower sides of the slot. The box hinge portion of the second member includes pivot points on the side surfaces, the side surfaces being the surfaces that oppose the upper and lower sides of the slot. The pivot points of the first box hinge portion mate with the pivot points of the second box hinge portion and thereby allow the hinge to open and close. The width of the first elongated member is larger than the width of the second elongated member at either end of the box hinge portion. In this embodiment, the outside overall width of the first elongated member including the slot may also be slightly wider relative to conventional instruments. The slope of the side surfaces of the second elongated member is nearly flat, although there may be some tapering of the member between the box hinge portion and the handle end portion on one end of the box hinge and the box hinge portion and the working tip portion on the other end of the box hinge. Alternatively, the hinge portion may be formed by machining a hinge portion without any step between the handle end or tip end and box hinge portion to provide no snag inducing surfaces for a suture to catch on.

Further, in an embodiment of the invention, the pivot points of the first box hinge portion may be protrusions and the pivot points of the second box hinge portion may be depressions. The pivot points of the first and second box hinge portions may also be cylindrical in shape. In an alternate embodiment, the pivot points of the first box hinge portion may be depressions and the pivot points of the second box hinge portion may be protrusions. In this embodiment, the pivot points of the first and second box hinge portions may also be cylindrical, round, conical triangular, elliptical, or any other preferred shape. In either of these embodiments, the pivot points of the first and second box hinge portions may be located at approximately the center of the sides of the slot and of the side surfaces.

A health care professional can use medical or surgical instruments that incorporate a snag-free box hinge through methods that do not have to compensate for snagging sutures.

These and other features and advantages of the invention will be more fully understood from the following detailed description of the invention taken together with the accompanying drawings.

BRIEF DESCRIPTION OF THE DRAWINGS

In the drawings:

FIG. 1 is a perspective view of a prior art surgical instrument including a box hinge comprised of two hinged members, one having a slot with parallel sides and the other having a stepped down portion machined to fit within the parallel sides in a closed suture needle holding position, illustrating a suture being snagged on edges of the stepped down portion and other edges;

FIG. 2 is a perspective view of the prior art surgical instrument of FIG. 1 showing the edges in the member where snagging occurs;

FIG. 3 is an end view of the prior art surgical instrument of FIG. 2 wherein the working tip portions are open and spaced and illustrating steps in the hinged members around the box hinge portion;

DETAILED DESCRIPTION OF THE INVENTION

Figure 4:
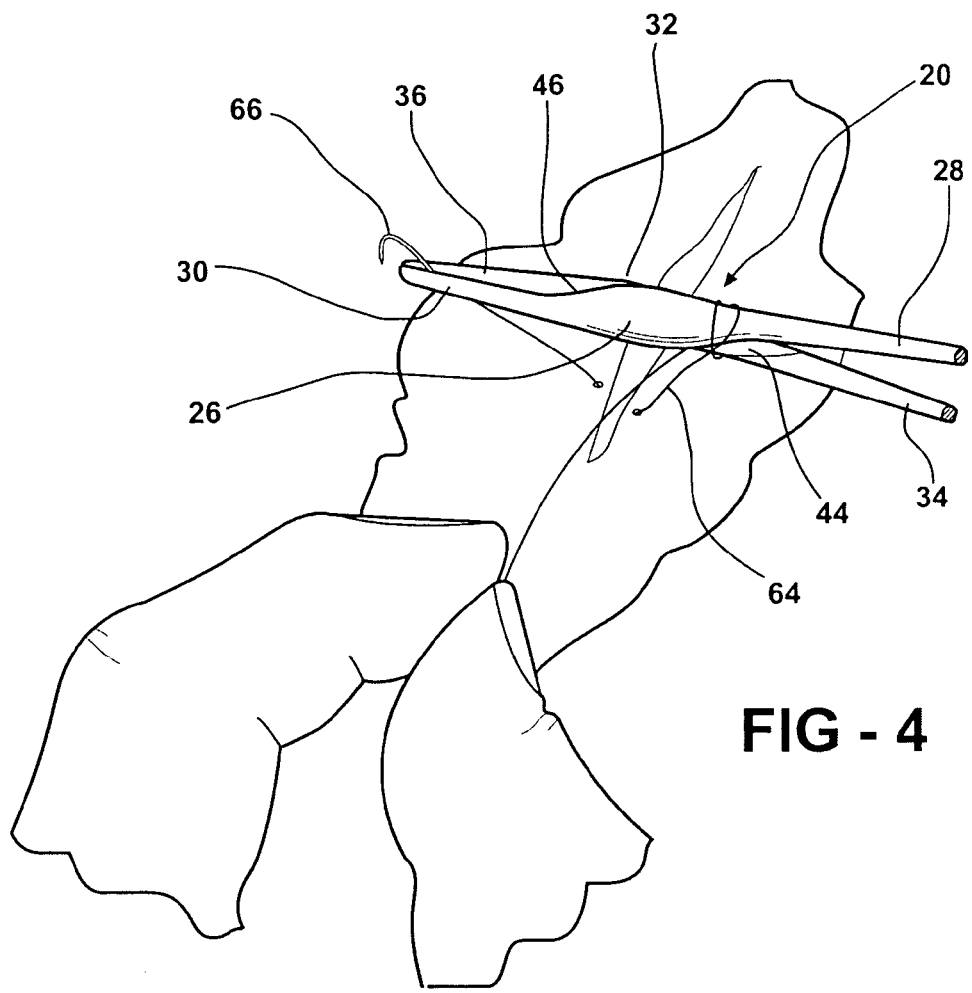
FIG. 4 is a perspective view of a surgical instrument including a snag free box hinge in accordance with the invention in an operative position mounting a suturing needle illustrating a surgeon's knot and an absence of edges on which the suture could snag.
Figure 5:
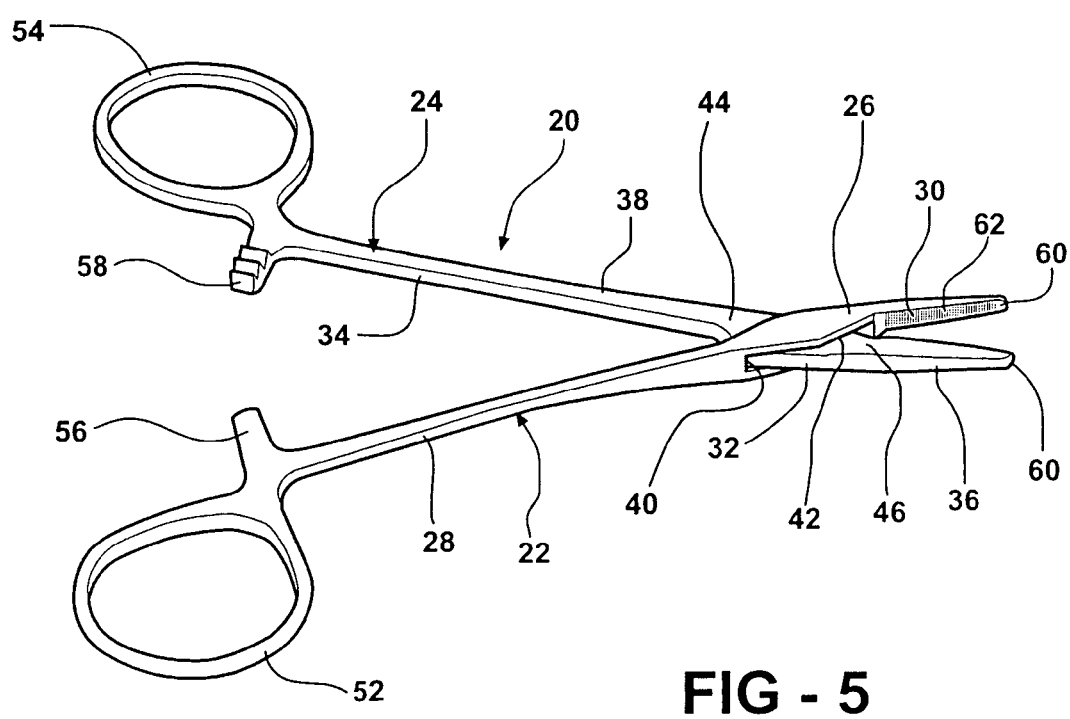
FIG. 5 is a perspective view of the surgical instrument of FIG. 4 illustrating a box hinge including two members, one having a slot with parallel sides and the other having a smooth, step-free portion.
Figure 6:
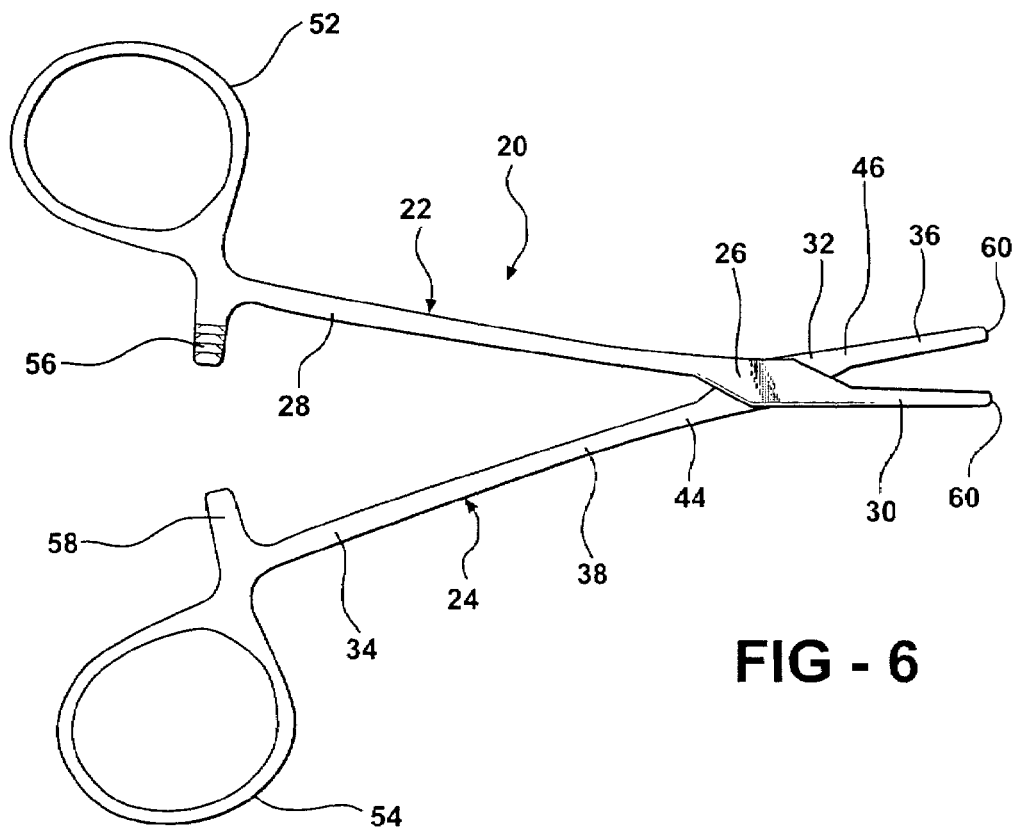
FIG. 6 is a plan view of the surgical instrument of FIG. 4 in the open position.
Figure 7:
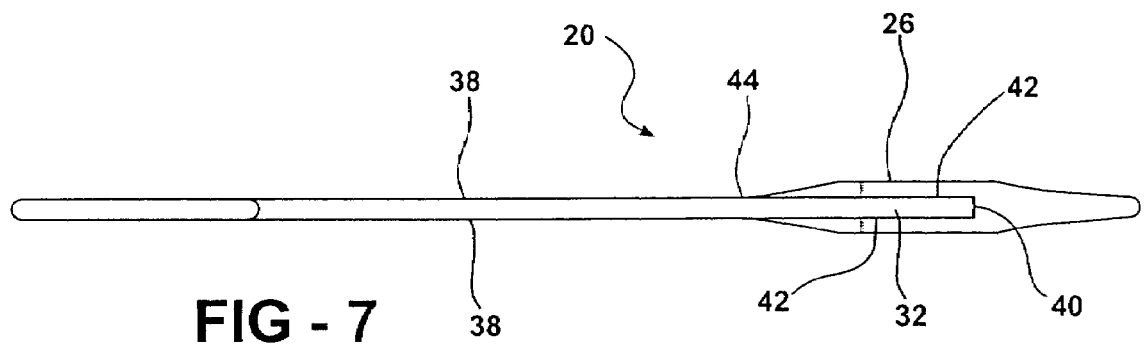
FIG. 7 is a side view of the surgical instrument of FIG. 4 in the open position.
Figure 8:
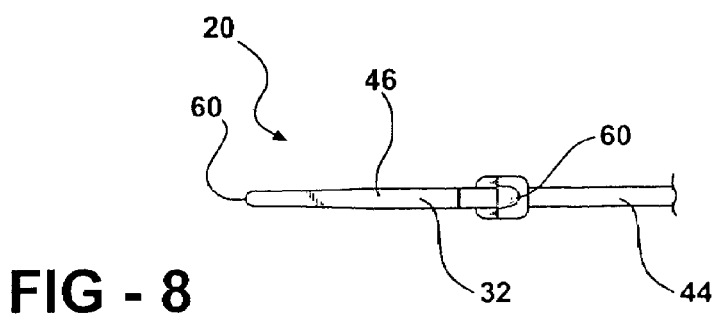
FIG. 8 is an end view of the surgical instrument including a snag free box hinge of FIG. 6 wherein the working tip portions are open and spaced and illustrating the absence of any step in the hinged members around the box hinge portion.

Referring now to FIGS. 4 through 10 of the drawings in detail, numeral 20 generally indicates a surgical instrument in accordance with a first embodiment of the present invention. As is more fully hereinafter described, the surgical instrument 20 provides for snag free movement of a suture along the box hinge portion of the surgical instrument as well as opening and closing of the box hinge without the use of a hinge pin.

As illustrated in FIGS. 4 through 10, a surgical instrument 20 includes a first elongated member 22 and a second elongated member 24. The first elongated member 22 includes a first box hinge portion 26, a handle end portion 28 and a working tip portion 30. The second elongated member 24 includes a second box hinge portion 32, a handle end portion 34 and a working tip portion 36. The second box hinge portion 32 has opposing side surfaces 38 that span the length of the second elongated member 24.

The first box hinge portion 26 includes a slot 40 having upper and lower sides 42 for receiving the second box hinge portion 32 therein. The second box hinge portion 32 has a cross-section generally conforming to the sides 42 of the slot 40. The second box hinge portion 32 illustrated is also generally the same width as the handle end portion 34 and the working tip portion 36 on either end 44, 46 of the box hinge portion 32 such that the slope of the side surfaces 38 of the second elongated member 24 from the handle end portion 34 through the second box hinge portion 32 to the working tip portion 36 is nearly flat. The result is that there are no steps on either end 44, 46 of the box hinge on which to snag a suture. This is in contrast to the machined portion of the prior art which results in steps $E_1$ and $E_2$. Alternatively, the second box hinge portion 32 can be disposed between handle end 34 and working tip 36 portions that therein provide a long smooth oblique transition, thereby being generally nearly flat and extending outward and away from the box hinge portion 32 toward the handle end portion 34 on one end 44 of the box hinge and the working tip portion 36 on the other end 46 of the box hinge.

Figure 9:
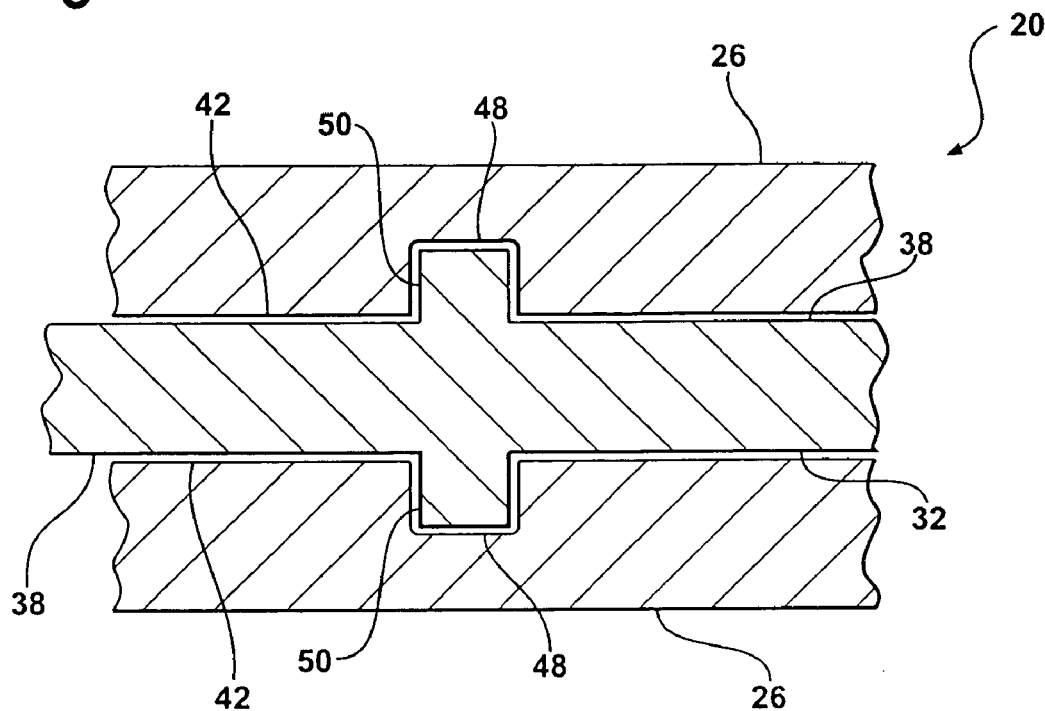
FIG. 9 is a side cutaway view of the box hinge portion of an embodiment of a surgical instrument in accordance with the present invention.
Figure 10:
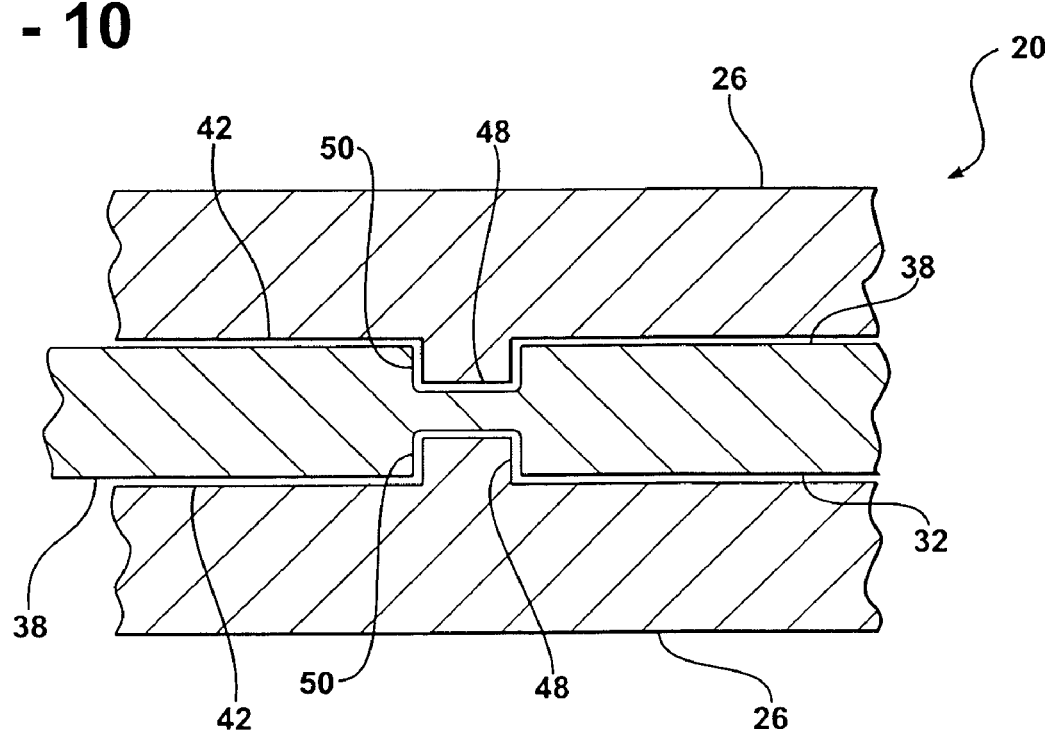
FIG. 10 is a side cutaway view of the box hinge portion of an alternate embodiment of a surgical instrument in accordance with the present invention.

Further, the slot 40 of the first box hinge portion 26 has a pivot point 48 on each of its upper and lower sides 42. The second box hinge portion 32 also has pivot points 50 on each of its side surfaces 38. The pivot points 48 of the first box hinge portion 26 mate with the pivot points 50 of the second box hinge portion 32, thereby allowing the box hinge to open and close. As shown in FIG. 9, the pivot points 48 of the first box hinge portion 26 may be protrusions while the pivot points 50 of the second box hinge portion 32 may be depressions. Alternatively, as shown in FIG. 10, the pivot points 48 of the first box hinge portion 26 may be depressions while the pivot points 50 of the second box hinge portion 32 may be protrusions. In either case as illustrated in FIGS. 9 and 10, the pivot points 48 and 50 may be cylindrical. The pivot points 48 and 50 may also be round, conical, triangular, elliptical, or any other preferred shape. Moreover, the pivot points 48 may be located at approximately the center of the sides 42 of the slot 40 while the pivot points 50 correspondingly may be located at approximately the center of the side surfaces 38 of the second box hinge portion 32.

The handle end portions 28, 34 include a circular handle 52, 54 and a cooperating locking mechanism 56, 58 disposed near the circular handles 52, 54 that are interconnectable to effectively lock the distal tip portions 30, 36 of the first and second elongated members 22, 24 in urged engagement. The inner working surfaces 60 of the working tip portions 30, 36 may include a plurality of ridges, or other grasping structures 62 that enhance the grip of the working tips 30, 36 when the surgical instrument 20 is in the operative position, as seen in FIG. 4.

In FIG. 4, an advantage of the surgical instrument 20 is shown. The surgical instrument 20 is in the operative position clamping a surgical suturing needle between the working tip portions 30, 36. A suture 64 attached to a needle 66 engaged between the working tips 30, 36 does not snag on the members at the ends 44, 46 between the box hinge portions 26, 32 and the handle end portions 28, 34 or the working tip portions 30, 36 respectively when the suture 64 is in contact with the surgical instrument 20, such as when a surgeon is tying a knot in the thread, or the instrument 20 is moving relative to and in contact with other suture threads disposed about an open wound.

The box hinge structure herein described can also be applied to numerous other types of non-needle holder surgical instruments, such as any manual surgical instrument, clamp type forceps, blood vessel clamps, and scissors that employ a box hinge. These instruments can be formed of stamped metal construction and can be readily disposable, or reusable, at manufacturer's and users option.

As an example of a suture needle holder application, a medical care provider uses the surgical instrument together with a suturing needle and suture thread to conduct suturing in a snag-free manner in accordance with the method in which a surgical instrument according to the invention is provided, a suture needle with suture thread is operatively mounted in the working tip portion of the instrument, and a wound or other opening in a patient is sutured in accordance with common medical practice.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A surgical instrument comprising:
   a first elongated member having a handle end portion, a working tip portion, and a box hinge portion between said handle and tip end portions;
   a second elongated member having a handle end portion, a working tip portion, and a box hinge portion between said handle and tip end portions, said second elongated member also having two opposing side surfaces;
   said first box hinge portion being defined by a slot having upper and lower sides for receiving said second box hinge portion therein, said slot having a pivot point on each of said upper and lower sides;
   said second box hinge portion being generally continuous in width with the handle and tip portions on either side of the box hinge portion; and
   said second box hinge portion having a pivot point on each of said side surfaces of the second box hinge portion;
   said pivot points of the first box hinge portion mating with said pivot points of the second box hinge portion;
   wherein said first box hinge portion pivot points and said second box hinge portion pivot points are one of either protrusions and depressions, respectively, and otherwise depressions and protrusions, respectively.

2. The surgical instrument of claim 1, wherein said first box hinge portion pivot points and said second box hinge portion pivot points are one of a cylindrical, round, conical, triangular, and elliptical shape.

3. The surgical instrument of claim 1, wherein said first box hinge portion pivot points and said second box hinge portion pivot points are located at approximately the center of the sides of the slot and of the side surfaces respectively.

4. The surgical instrument of claim 1, wherein the side surfaces of the second elongated member have a nearly flat transitional slope therebetween the box hinge portion and the handle end portion on one end and the box hinge portion and the working tip portion on the other end.

5. The surgical instrument of claim 1, wherein the transitional slope of the second elongated member between the box hinge portion and the handle end portion on one end and the box hinge portion and the working tip portion on the other end is a long smooth oblique transition.

6. The surgical instrument of claim 1, wherein the first elongated member is wider than the second elongated member at either end of the box hinge portion.

7. The surgical instrument of claim 1, wherein the handle end portion includes a circular handle and a locking mechanism interconnected at the far end of the handle end portion.

8. The surgical instrument of claim 1, wherein the inside surface of the working tip portion includes a gripping structure.

9. The surgical instrument of claim 1, wherein the length of the handle end portion is generally longer than the length of the working tip portion.

10. An improved surgical instrument of the type having two elongated members, each member having a working tip portion, a handle end portion, and a box hinge portion, wherein the improvement comprises a box hinge defined by a slot located in the box hinge portion of the first elongated member having upper and lower sides for receiving the box hinge portion of the second elongated member therein, the slot having pivot points on each of its upper and lower sides and the second box hinge portion having pivot points on each of its side surfaces, one set of either the first or second box hinge portion pivot points being protrusions and the other being depressions, the pivot points of the first box hinge portion mating with the pivot points of the second box hinge portion such that the box hinge may open and close, and the ends of the second box hinge portion having a width narrower than the width of the ends of the first box hinge portion, such that the side edges of the first elongated member are larger relative to the side edges of the second elongated member at either end of the box hinge.

* * * * *